(12) United States Patent
Aasmul

(10) Patent No.: US 7,541,598 B2
(45) Date of Patent: Jun. 2, 2009

(54) METHOD AND APPARATUS FOR MEASURING THE PHASE SHIFT INDUCED IN A LIGHT SIGNAL BY A SAMPLE

(75) Inventor: Søren Aasmul, Holte (DK)

(73) Assignee: Precisense A/S, Horsholm (DK)

( * ) Notice: Subject to any disclaimer, the term of this patent is extended or adjusted under 35 U.S.C. 154(b) by 0 days.

(21) Appl. No.: 11/658,263

(22) PCT Filed: Jul. 27, 2005

(86) PCT No.: PCT/EP2005/008147

§ 371 (c)(1),
(2), (4) Date: Mar. 8, 2007

(87) PCT Pub. No.: WO2006/010604

PCT Pub. Date: Feb. 2, 2006

(65) Prior Publication Data

US 2008/0024779 A1 Jan. 31, 2008

(30) Foreign Application Priority Data

Jul. 27, 2005 (GB) .................................. 0416732.6

(51) Int. Cl.
*F21V 9/16* (2006.01)
(52) U.S. Cl. .................................................. 250/458.1
(58) Field of Classification Search ................ 250/458.1
See application file for complete search history.

(56) References Cited

U.S. PATENT DOCUMENTS

| | | | | |
|---|---|---|---|---|
| 5,184,618 A | * | 2/1993 | Wider et al. | ................. 600/317 |
| 5,216,483 A | | 6/1993 | Berthold et al. | |
| 5,617,205 A | * | 4/1997 | Dou et al. | .................... 356/301 |
| 5,757,013 A | | 5/1998 | Groger et al. | |
| 6,316,774 B1 | * | 11/2001 | Giebeler et al. | .......... 250/458.1 |
| 7,106,425 B1 | * | 9/2006 | Bultman et al. | ................ 356/73 |

(Continued)

FOREIGN PATENT DOCUMENTS

EP  0 442 295 A  8/1991

(Continued)

OTHER PUBLICATIONS

International Search Report of PCT/EP2005/008147, mailed Oct. 14, 2005.

*Primary Examiner*—David P Porta
*Assistant Examiner*—Kiho Kim
(74) *Attorney, Agent, or Firm*—Nixon & Vanderhye P.C.

(57) ABSTRACT

A first light source emits a light signal along a measurement optical path that includes a sample and a second light source emits a light signal along a dummy measurement optical path. A measurement circuit receives the light signals and provides outputs separated in time which are indicative of the phase of the respective light signals. A phase shift is induced in light in the measurement optical path by the sample. A reference circuit receives a signal indicative of the phase of the light signals emitted by the first and second light sources. Circuitry compares the phases of light output from the two circuits to provide output indicative of a first measured phase difference during operation of the first light source. Correction is applied to this measurement by taking a similar phase difference measurement during operation of the second light source and comparing the two phase differences.

22 Claims, 11 Drawing Sheets

U.S. PATENT DOCUMENTS

2004/0090622 A1    5/2004    Nielsen et al.
2004/0114137 A1    6/2004    Mader et al.
2005/0062969 A1*   3/2005    Harju et al. ................. 356/417

FOREIGN PATENT DOCUMENTS

| EP | 0 442 295 A2 | 8/1991 |
| EP | 0 453 599 A | 10/1991 |
| EP | 0 453 599 A1 | 10/1991 |

* cited by examiner

METHOD AND APPARATUS FOR MEASURING THE PHASE SHIFT INDUCED IN A LIGHT SIGNAL BY A SAMPLE

This application is the US national phase of international application PCT/EP2005/008147, filed 27 Jul. 2005, which designated the U.S. and claims priority of FR 0416732.6, filed 27 Jul. 2004, the entire contents of each of which are hereby incorporated by reference.

The present invention relates to a method and apparatus for measuring a phase shift induced in a light signal by a sample.

In conventional fluorescence microscopy, the intensity distribution of the emission of a fluorophore is recorded. Another parameter that can be measured is "fluorescence lifetime". When a fluorophore is excited by a light pulse, the emission shows a decay (typically in the order of nano-seconds). This decay time, referred to as fluorescence lifetime is characteristic of the fluorophore, as well as its state.

Fluorescence lifetime sensing is a powerful method to measure energy transfer efficiency in fluorescence resonance energy transfer (FRET) assays. FRET is a distance-dependent interaction between the excited states of two dye species in which excitation energy is transferred from a donor to an acceptor without emission of a photon. The efficiency of FRET is inversely dependent on the sixth power of the intermolecular separation. Detection of FRET can therefore be used to determine the distance between a species labelled with the donor and a species labelled with the acceptor. This may be used for example to determine whether the two species are bound to one another.

In a competitive assay based on FRET, FRET can occur as a result of a FRET active molecule combining with a competition agent that is also FRET active. The competition agent competes with FRET inactive material (an analyte), which when combined with the FRET active molecule, will not cause FRET. Each of the competition agent and the analyte binds reversibly to the FRET active material for a finite amount of time. This means that both the competition agent and analyte have opportunities to bind with the FRET active material to reach equilibrium. As the amount of competition agent present in such an assay is predetermined, the amount of FRET occurring can be used to calculate the concentration of analyte present. When no analyte is present, a 100% of the possible FRET will occur.

When an excitation light is modulated at sufficiently high frequency, a FRET signal can be detected not only by the intensity of the fluorescence, but also in the phase shift between the excitation light and the emitted fluorescence.

However, it is difficult to get an accurate reading of the phase shift caused by fluorescence as the measured phase of a light signal may drift as a result of factors affecting the sensor's electronics, such as the measuring electronics having been subjected to temperature changes and ageing.

Attempts have been made to measure accurately the shift in phase caused by fluorescence with the use of phase fluorometers. Commercially available phase fluorometers, as shown in FIG. 1, sometimes have two identical signal branches, a sample signal branch 201 and a reference signal branch 203. Excitation light 209 is generated by a light source 205 to be radiated upon a fluorescent sample 207. A small portion 211 of this excitation light is split out before the sample 207 to illuminate a detector 213 in the reference branch 203. The phase of the light detected in the reference signal branch 203 is compared with the phase of the fluorescent light emitted from the sample 207 to give the phase difference between the reference and sample branches. This gives an initial measurement of the shift in phase induced as a result of fluorescence of light in the sample signal branch. The phase measurement compensates for phase drift in the light source or light source driving circuitry, but does not account for the phase drift that may be caused by the electronic circuitry.

Shortly before and after illumination of the fluorescent sample 207, the fluorescent sample is replaced with a reference object 215 that does not fluoresce when excitation light is radiated upon it. As previously, the excitation light 209 is generated by the light source to radiate the reference object. A small portion of the excitation light is split out before the reference object to illuminate the detector on the reference branch. The phase of the light detected in the reference signal branch is compared with the phase of light detected in the sample branch to provide a calibration for the final signal measured when the sample object fluoresces. Any difference in phase between the signals detected by the sample branch and reference branch in this case will be due to differences in the electronics or to differences in the respective path lengths.

The phase lag induced by the fluorescent sample object is finally calculated by comparing the phase difference between the two branches when fluorescence occurs and the phase difference between the two branches when fluorescence does not occur.

This eliminates phase drifting caused by the electric components and accounts for any difference in phase that might be caused by the optical path the light follows.

The system described above requires a motorised or manually driven mechanism for changing the object from the sample object to the reference object. At this time, it becomes necessary to change the filters receiving light reflected from the reference object due to its non-fluorescent nature. Furthermore, it may be necessary to change the filters in the optical paths to adapt to the different light intensities. This would also need to be done using a motorised, mechanical system. This sort of system is undesirable as it is ultimately expensive, space consuming, complex to produce and is prone to damage as a result of the moving parts. Furthermore, it may be desirable to miniaturize a system as described above to enable use of such a system for medical purposes, e.g. for continuous blood glucose measuring. In applications such as these where the phase fluorometer would be worn by man, it would be undesirable to use motors that cause excessive vibrations and noise.

The object of this invention is to provide a system and method of measuring the difference in phase including correction for electronic drift performed without the need for manual or mechanical intervention.

According to a first aspect of the present invention, apparatus is provided for measuring a phase shift induced in a light signal by a sample, the apparatus comprising:

a first light source for emitting a light signal along a measurement optical path, wherein the measurement optical path includes a sample location;

a second light source for emitting a light signal along a dummy measurement optical path, the first and second light sources being arranged for alternate operation;

a measurement electronic circuit for receiving the light signals from the measurement and dummy measurement optical paths, the measurement electronic circuit being arranged to provide outputs separated in time which are respectively indicative of the phase of the light signals received from each of the measurement and dummy measurement optical paths, wherein in use a phase shift is induced in light in the measurement optical path by a sample in said sample location such that the phase of light of the first light source received from the measurement optical path is different to the phase of light emitted from the first light source;

a reference electronic circuit for receiving a signal indicative of the phase of the light signals emitted by the first and second light sources;

circuitry to compare the phase of light indicated by the output of the measurement electronic circuit responsive to the first light source with the phase of light indicated by the reference electronic circuit to provide an output indicative of a first measured phase difference and to compare the phase of light indicated by the output of the measurement electronic circuit responsive to the second light source with the phase of light indicated by the reference electronic circuit to provide an output indicative of a second measured phase difference, and circuitry to apply a correction to the first measured phase difference on the basis of the second measured phase difference to correct for errors in said first measured phase difference due to phase changes induced by said measurement and reference electronic circuits so as to obtain an improved measurement of the shift, in phase induced in the light of the first light source by the sample.

Preferably, the measurement optical path comprises a beam splitter receiving light from said first light source and reflecting said light toward said sample location and receiving fluorescence emission light in use emitted from said sample location and transmitting said fluorescence emission light to said measurement electronic circuit.

More preferably, the measurement optical path comprises an excitation filter arranged to select a wave length of light suitable for exciting a fluorescent sample at said sample location and an emission filter suitable for selecting a wave length of fluorescent light emitted from said sample location.

An oscillator is coupled to each of the first and second light sources to produce light signals of oscillating intensity. A drive current fed into each of the first and second light sources to produce light signals of oscillating intensity is generated by direct digital synthesis.

In one embodiment, the dummy measurement path comprises the beam splitter, the beam splitter being arranged to receive light from the second light source, reflect said light toward said sample location, receive said light reflected from said sample location and transmit the light to said measurement electronic circuit.

Preferably, the dummy measurement optical path further comprises the said emission filter for selecting a wavelength of light comparable to the wavelength of fluorescent light emitted from the sample location.

In an alternative embodiment, light from the second light source is not received by the beam splitter and is guided directly to the measurement electronic circuit.

Accordingly, the dummy measurement path further comprises an electro-optical attenuator for reducing the intensity of light emitted from the second light source.

In a preferred embodiment, the light in the dummy measurement path does not include a wave length of light suitable for exciting the fluorescent sample.

In one embodiment, light emitted from said first and second light sources is of the same wavelength and the dummy measurement path further comprises a filter to eliminate light of the wavelength suitable for exciting the fluorescent sample.

In an alternative embodiment, the first light source and the second light source emit light of different wavelengths, and the light emitted from the second light source does not include a wavelength suitable for exciting the fluorescent sample.

Preferably, the measurement electronic circuit comprises an opto-electric converter for receiving light signals from said measurement path and the dummy measurement path, wherein the opto-electric converter outputs an electrical signal corresponding to an intensity of the light illuminating it.

More preferably, the opto-electric converter of the sample circuit is an avalanche photo-diode, whereby a bias voltage is provided to the avalanche photo-diode to enhance the electrical signal corresponding to the intensity of the light illuminating the avalanche photo-diode.

Means are provided for guiding light from the first and second light sources along the reference and dummy reference optical paths respectively to an opto-electric converter of the reference circuit.

Preferably, the opto-electric converter of the reference circuit is a photo-diode.

In a preferred embodiment, the system further comprises electronic circuitry for modulating the signal being processed in each of the measurement circuit and the reference circuit to produce an output representing the phase of the signal being processed.

Preferably, the electronic circuitry modulating the signal in each of the measurement and reference circuit comprises a mixer in each of the measurement electronic circuit and the reference electronic circuit, each mixer being coupled to a further oscillator.

In one embodiment, a signal having a modulated frequency of from 0.1 to $10^3$ megahertz is output from the further oscillator, and is combined with the signal in each of the measurement and reference circuits by means of the respective mixers and a modulated frequency of the light output from each said light source differs from said modulated frequency by an amount, which is from $10^2$ to $10^5$ hertz (heterodyne detection).

The measurement electronic circuit and the reference electronic circuit each further comprise a band pass filter, wherein the high frequency component of the output from each of the mixers of the measurement circuit and the reference electronic circuit is eliminated by the band pass filter.

In an alternative embodiment, a signal having a modulated frequency the same as the modulated frequency of light output from each light source is output from the further oscillator, and is combined with the signal in each of said measurement and reference circuits by means of the respective mixers (homodyne detection).

In a further embodiment, a modulated frequency of the light output from each light source is from 10 to $10^5$ hertz.

Preferably, the opto-electric converter of each of the measurement and reference electronic circuits is arranged to output an electronic signal to an amplifier which produces a voltage output, the respective mixers being arranged to receive said voltage outputs and the signal of modulated frequency from the further oscillator to produce a beat frequency output representing the frequency difference between said inputs, said output being indicative of the phase of the light received at the opto-electronic converter.

The further oscillator providing the predetermined frequency to the mixers of each of the measurement and reference circuit is a voltage controlled crystal oscillator.

Preferably, the predetermined frequency to the mixers of each of the measurement and reference circuit is generated by direct digital synthesis.

In a preferred embodiment, the band pass filter of each of the measurement and reference electronic circuits are respectively arranged to receive the beat frequency output from each mixer to reduce noise in the respective signal.

Preferably, the measurement and reference electronic circuits each further comprise an amplifier to amplify the filtered signal from the band pass filter and an analogue to digital converter for digitising the amplified signal.

In a preferred embodiment, a signal processing and control unit is provided to receive the digitised outputs from each of the measurement circuit and the reference circuit, the signal processing and control unit comprising further circuitry to compare the digitised signals received during operation of the first and second light sources respectively and to calculate the phase change induced by the sample. A result of the calculation is output to a display.

Preferably, the signal processing and control unit is arranged to control alternate operation of the first and second light sources, the frequency of the further oscillator, and the bias voltage provided to the avalanche photo-diode.

In one embodiment, two different frequencies of light are alternately generated and output from each of the first and second light sources consecutively to enable further calculations.

The present invention also extends to a method of measuring a phase shift induced in a light signal by a sample, comprising the steps of:

emitting a first light signal along a measurement optical path, wherein the measurement optical path includes a sample location;

emitting a second light signal along a dummy-measurement optical path, the first and second light signals being emitted alternately;

receiving in a measurement electronic circuit light signals from the measurement and dummy-measurement optical paths;

providing outputs separated in time from the measurement electronic circuit, wherein the outputs are respectively indicative of the phase of the light signals received from each measurement and dummy-measurement optical path;

receiving in a reference electronic circuit a signal indicative of the phase of the first and second light signals;

comparing the phase of light indicated by the output of the measurement electronic circuit and responsive to the first light signal with the phase of light indicated by the reference electronic circuit;

providing an output indicative of the first measured phase difference;

comparing the phase of light indicated by the output of the measurement electronic circuit in response to the second light signal with the phase of light indicated by the reference electronic circuit;

providing an output indicative of a second measured phase difference;

applying a correction to the first measured phase difference on the basis of the second measured phase difference to correct errors in said first measured phase difference due to phase changes induced by said measurement and reference electronic circuit so as to obtain an improved measurement of the shifting phase induced in the light of the first light source by the sample.

Embodiments of the invention will hereinafter be described with reference to the accompanying drawings, in which.

Figure 1:
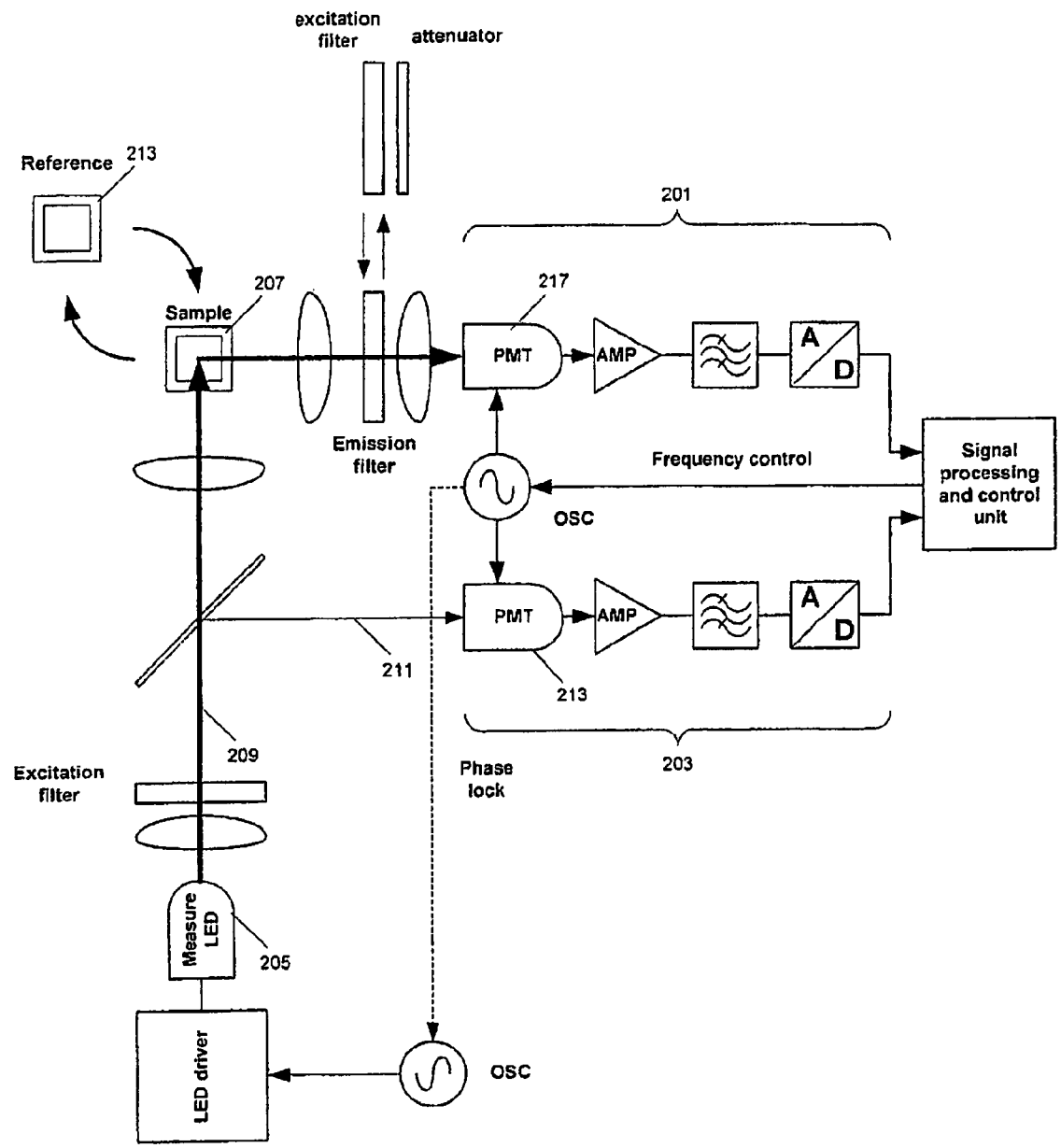
FIG. 1 is a schematic diagram of a commercially available fluorometer.
Figure 2:
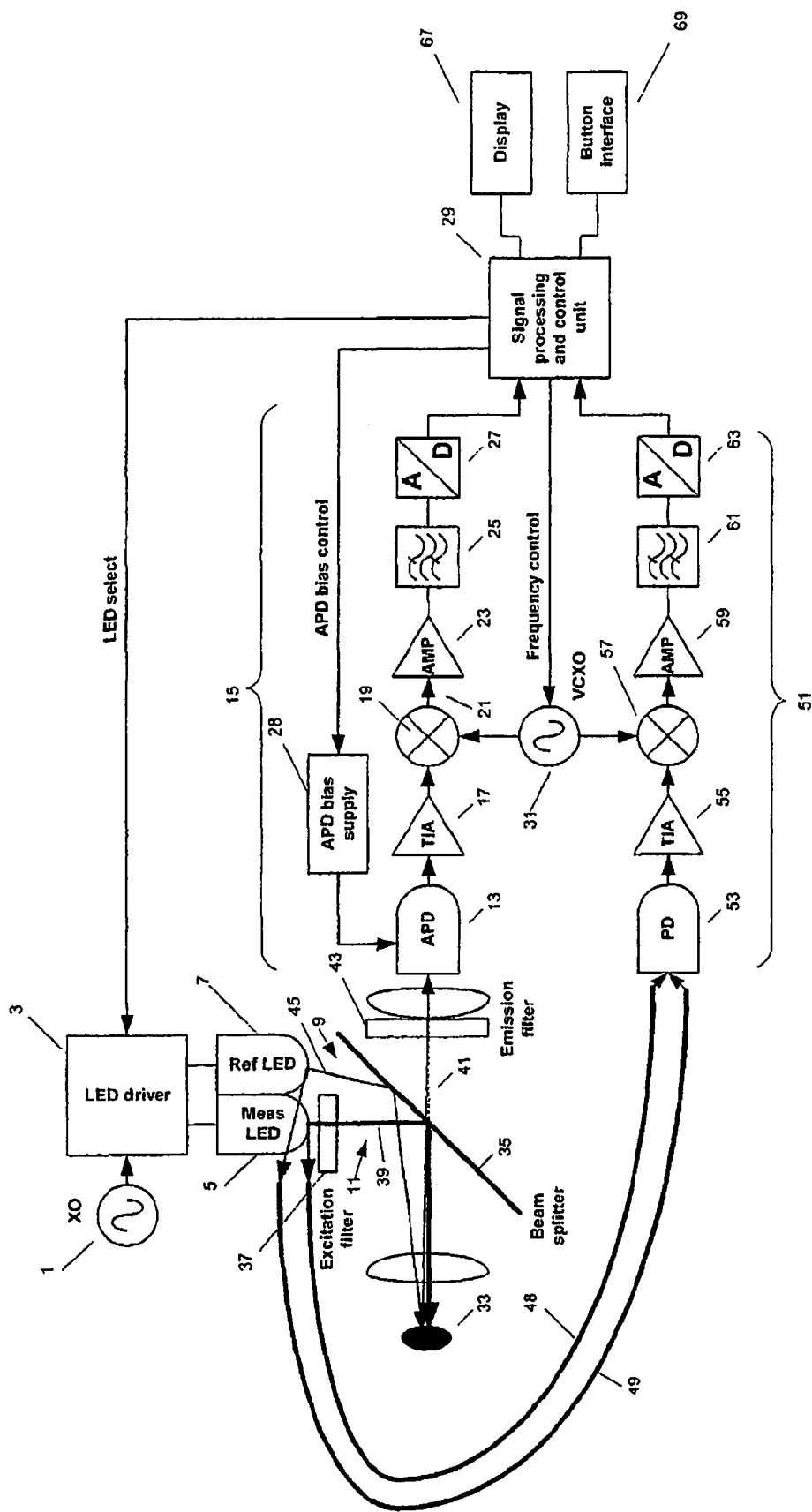
FIG. 2 is a schematic diagram of one embodiment of the present invention.

Shown in FIG. 2 are the various components of an embodiment of the present invention. The system includes a crystal oscillator 1 coupled to a LED driver 3, two LEDs 5, 7, which can be activated one at a time, and an excitation filter 37. Light from each of the LEDs 5, 7 is directed simultaneously to a measurement circuit 15 and a reference circuit 51. Light from both LEDs 5, 7 is directed by means of a beam splitter 35.

The measurement circuit 15 comprises an emission filter 43, avalanche photo diode 13, trans-impedance amplifier 17 for converting the current signals received to voltage signals, mixer 19, amplifier 23, band pass filter 25, an analogue to digital converter 27 and an avalanche photo diode bias supply 28.

Similarly, the reference circuit 51 comprises a photo diode 53, a trans-impedance amplifier 55, a mixer 57, an amplifier 59, a band pass filter 61 and an analogue to digital converter 63. Both the reference and measurement circuits are further provided with a signal processing and control unit 29 to process the information from both circuits, a further crystal oscillator 31, a display unit 67 to display results, and an interface 69 having at least two buttons.

Although the invention has been described with respect to the use of light emitting diodes, it will be appreciated that other light sources could be used, for example, laser diodes.

In operation, the LED driver 3 is coupled to the crystal oscillator 1 and is arranged to produce a light signal from each of the first and second LEDs 5, 7 respectively. In this embodiment, a sinusoidal light signal is produced by means of the crystal oscillator 1. It should be clear, however, that provided a phase of the light signals can be determined, other methods known in the art may be suitable, for example, by generating a light signal having a square pulse.

Figure 8:
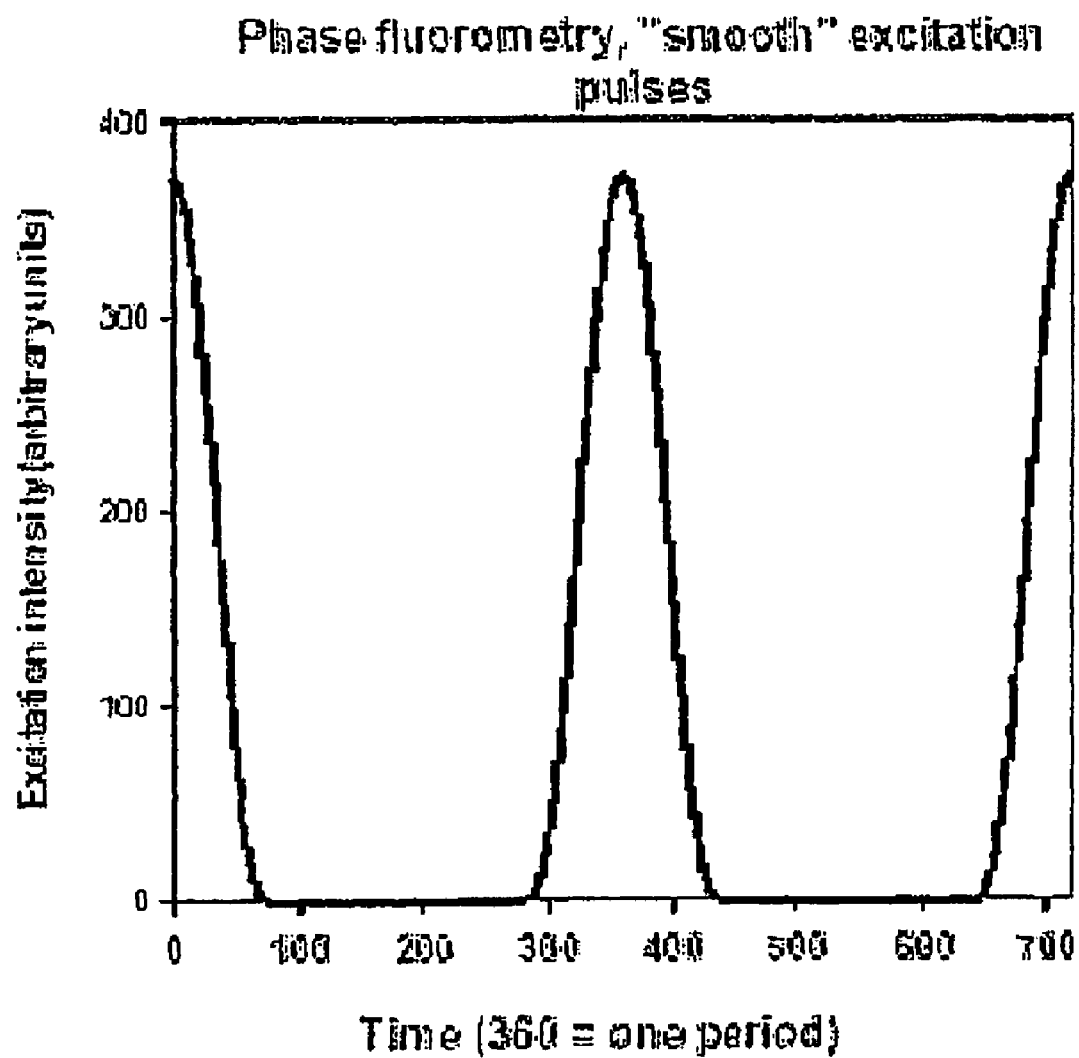
FIG. 8 shows a graph of the smooth excitation pulse used in an embodiment of the present invention.
Figure 9:
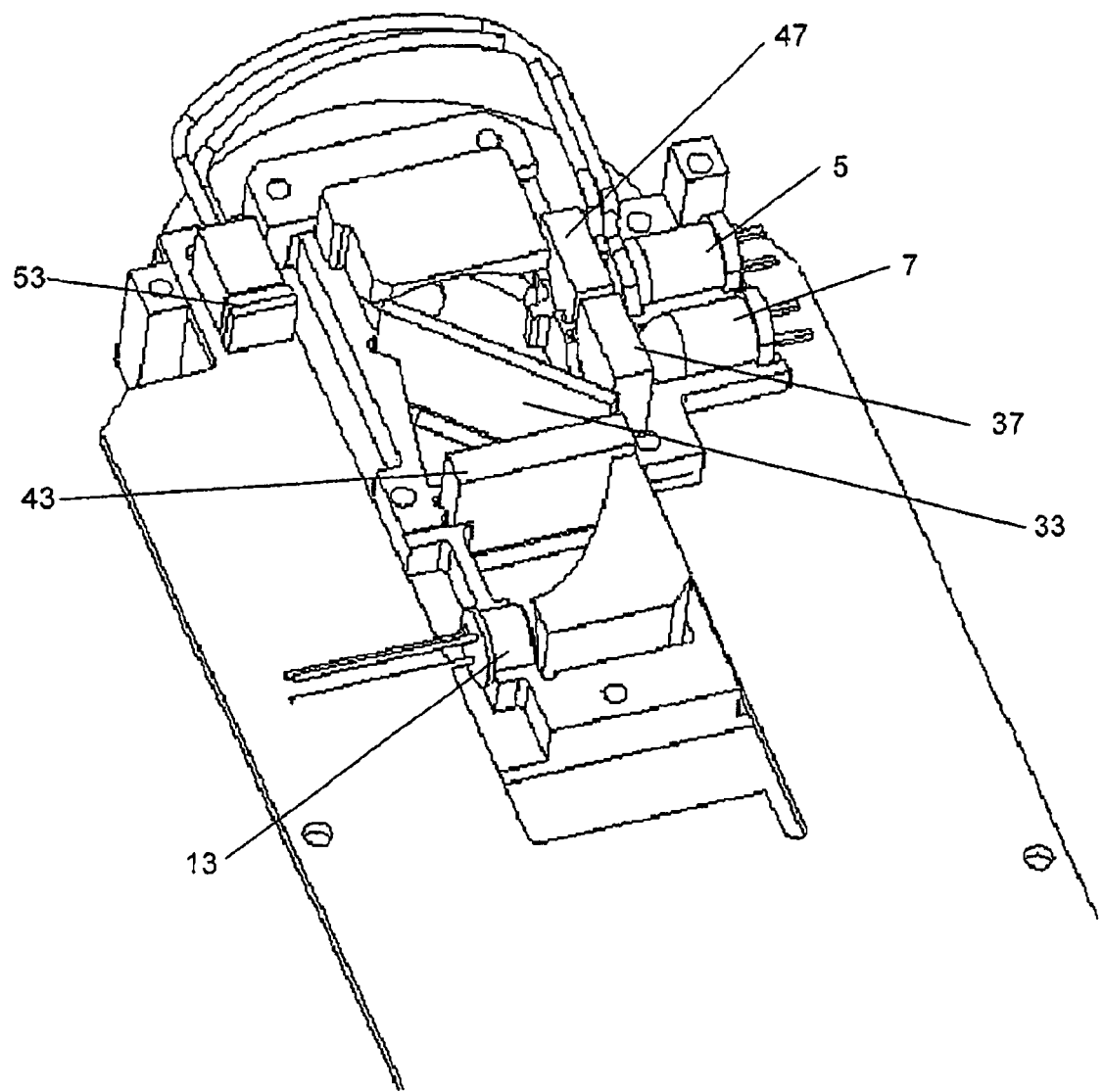
FIG. 9 shows a plan view of the apparatus of the invention.
Figure 10:
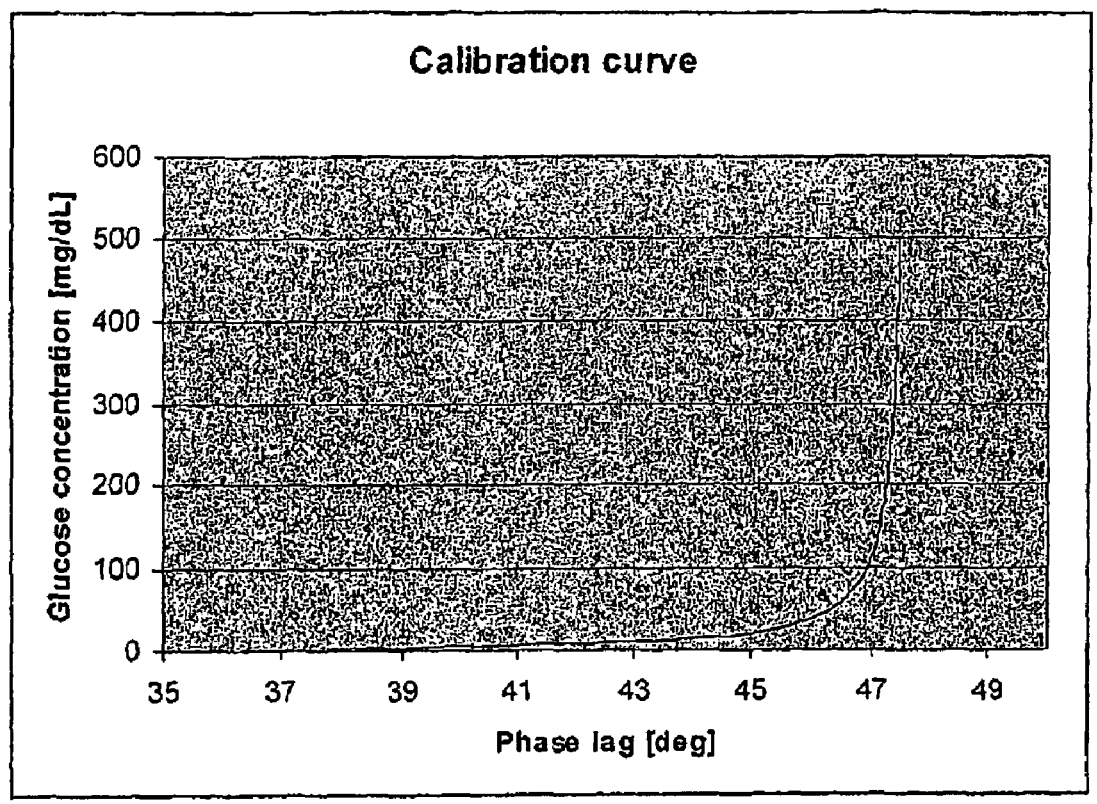
FIG. 10 shows a calibration curve for use in real operation.

For example, in one embodiment, the light signal generated and emitted from each of the first and second light LEDs has a smooth excitation pulse. As shown in FIG. 8, the positive pulses are narrower than that of a sinusoidal waveform so that the overall shape of the pulse is approximately Gaussian.

As set out in the paper "Theoretical investigation of the signal-to-noise ratio for different fluorescence lifetime imaging techniques" by CARLSSON K. PHILLIP J, Proc SPIE 4611, 70-78, 2002, Dirac pulse excitation is the most favourable excitation method for use with a fluorophore. Dirac pulses are infinitely narrow and a Dirac excitation signal yields a nominal figure of merit (F) of 1. Such pulse excitation is, however, hard to produce in practice.

The signal to noise ratio (SNR) is reversly proportional to F squared. Therefore, an optimum SNR is achieved when F=1. Sinusoidal modulation yields a figure of merit of 4, and as such, sinusoidal modulation is 16 times less favourable than Dirac modulation in terms of SNR. However, sinusoidal modulation is easier to produce as there is a lower demand for bandwidth and power consumption.

As set out by Carlsson, a smooth excitation pulse gives a figure of merit of 1.55, which corresponds to a SNR reduction of 2.4 times compared to the Dirac pulse excitation. This is therefore more favourable than a standard sinusoidal signal.

Figure 11:
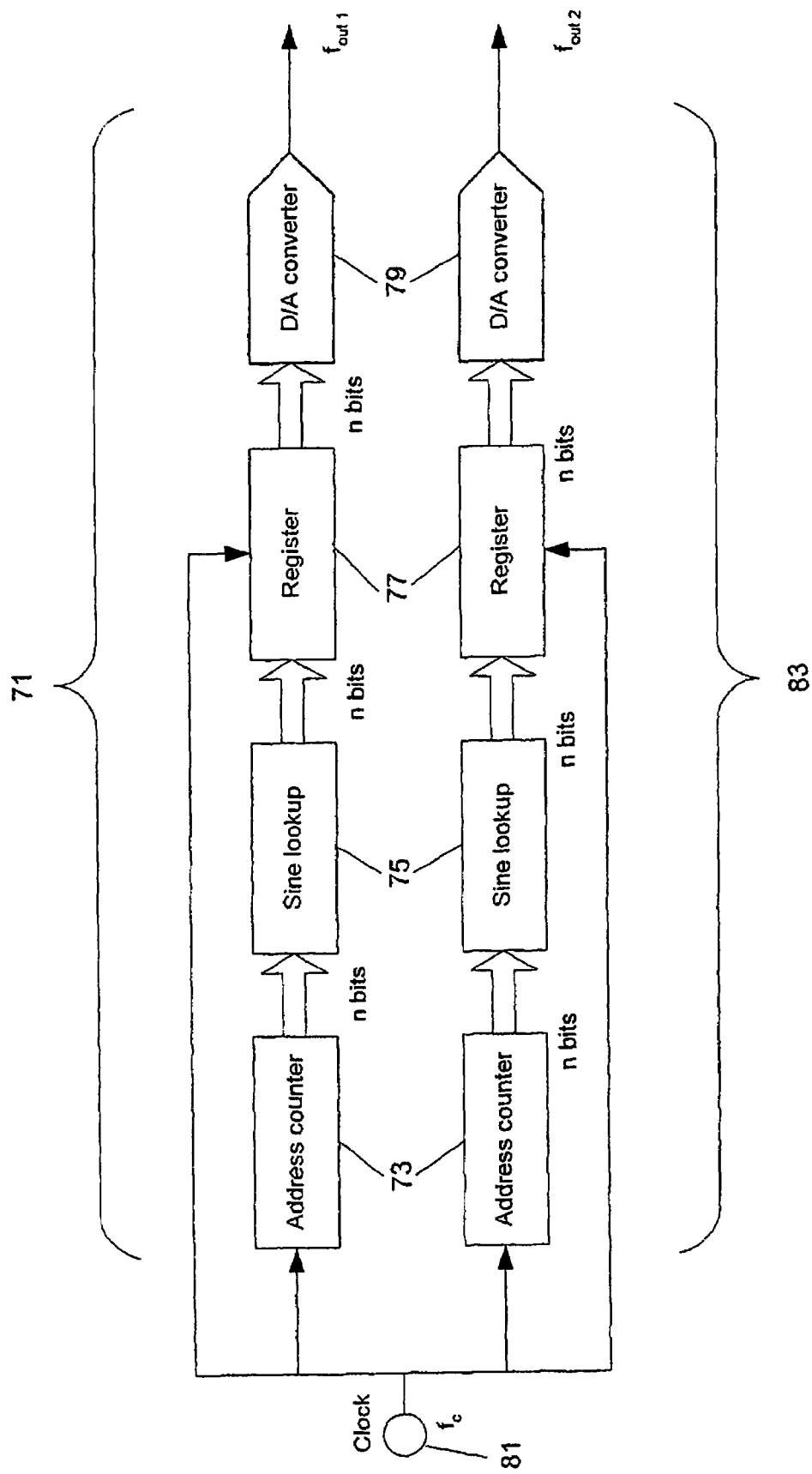
FIG. 11 shows a schematic diagram of two parallel direct digital synthesisers.

Direct digital synthesis may be used to generate the sinusoidal waveform as well as the smooth pulse excitation. As shown in FIG. 11, a direct digital synthesiser 71 consists of an address counter 73, a programmable read only memory (PROM) 75 that is used to store various waveforms, a register 77 and a digital to analogue converter 79.

Digital amplitude information that corresponds to a complete cycle of a sine wave is stored in the PROM 75, which functions as a sine look-up table. The address counter steps through and accesses each of the PROM's memory locations and the contents, the equivalent sine amplitude words, are presented to a high speed digital to analogue converter 79. The digital to analogue converter generates an analogue sine wave in response to the digital input words from the PROM. The rate at which the synthesiser completes one wave governs the frequency. A clock 81 is provided by the signal processing and control unit 29.

The LED driver 3 is controlled by the signal processing and control unit 29 such that the first LED 5 (hereinafter referred to as "the measurement LED") and the second LED 7 (hereinafter referred to as "the reference LED") are switched on and off alternately such that only one out of the measurement 5 or reference LED 7 is active at any one time. A light signal is therefore alternately emitted from the measurement LED 5 and the reference LED 7.

In the embodiment shown in FIG. 2, light from the measurement LED 5 is directed along two different paths, a first optical path 11, and a first reference path 48. Similarly, light from the reference LED 7 is directed along two different paths, a second optical path 9, and a second reference path 49. The first optical path 11 and the second optical path 9 follow a similar route to lead to the avalanche photo-diode (APD) 13 of the sample circuit 15.

Similarly, the first reference path 48 and the second reference path 49 follow a similar route to lead to the photo-diode 53 of the reference circuit 51.

Light in the first optical path passes through the excitation filter 37 and is directed by means of the beam splitter 35 onto a fluorescent sample 33. The light (excitation light) 39 in the first optical path is passed through the excitation filter 37 to ensure that it has stable spectral characteristics. The excitation light 39 causes excitation of the sample such that it emits a fluorescent light 41 having a different phase, spectrum and intensity to the light 39 emitted from the measurement LED 5.

The fluorescent light 41 is then passed through the emission filter 43 before illuminating the APD 13 of the sample circuit 15. The signal is then processed by the sample circuit 15 such that the phase of fluorescent light 41 detected by the APD 13 can be determined.

Simultaneously, light 39 from the measurement LED 5 is guided along the reference path 48 to the photo-diode 53 of the reference circuit 51, such that the phase of the reference light can be determined. The phase of the light received at the reference circuit 51 should be the same as that emitted from the measurement LED 5.

The phase of light determined in each of the sample circuit 15 and the reference circuit 51 is compared, to determine a phase shift induced in the first optical path 11. It is expected that the main shift in phase along the first optical path 11 is caused by the fluorescent sample 33. However, this measurement can not be considered to be absolute, since the electronics in each circuit may cause varying degrees of drift in phase as a result of ageing of the electronics or temperature changes.

To determine an absolute shift in phase caused by the fluorescent sample 33, it is necessary to correct for such drift caused by the electronics of the system. To enable this, immediately before and after activation of the measurement LED 5, the reference LED 7 is activated. A portion of light emitted from the reference LED 7 is directed along the reference path 49 to the reference circuit 51. The remainder of the light emitted from the reference LED 7 is directed along the second optical path 9 towards the measurement circuit 15.

In this embodiment, to enable correction, the light in the second optical path does not cause the fluorescent sample to excite. This can be achieved in two ways. As shown in FIG. 2, the light 45 emitted from the reference LED 5 is directed by means of the beam splitter 35 towards the fluorescent sample 33.

In one embodiment, the light emitted from the reference LED 7 is of a different wavelength to that emitted from the measurement LED 5. Specifically, the light from the reference LED 7 is situated spectrally in the pass band of the emission filter 43 such that the light is scattered or reflected from the sample site. In an alternative embodiment, the light emitted from both the measurement LED 5 and the reference LED 7 is of the same wavelength. In this embodiment (not shown), a further filter is provided prior to illumination of the sample site to exclude those wavelengths required for exciting the sample.

As previously, the signal in the measurement branch is compared to that detected in the reference branch. In ideal conditions, the phase difference between the two detected signals is representative of the phase change introduced by the sample. In real operation, however, the degree of drift in phase caused by the electronic circuitry will vary between the measurement and reference branches. As almost no time elapses between measurement of the signals during operation of the measurement LED 5 and during operation of the reference LED 7, it is assumed that the condition of the circuitry in both the measurement and reference branches will not have varied significantly between readings.

Therefore, it is assumed that any difference in phase detected between the sample and measurement branches during operation of the reference LED 7 is caused by the electronics and differences in the respective path lengths.

It is appreciated that there is a minor variation in path length from the measurement LED 5 to the APD 13, and from the reference LED 7 to the APD 13. However, this is constant, i.e. the difference in the respective path lengths will always remain the same, resulting in a constant phase offset which easily may be corrected for. The avalanche photo-diode (APD) 13 of the sample circuit is reverse biased with a high voltage. This causes an amplification of the initial photo current of typically between 50 and 500. The light signal fed into the APD 13 is very weak and in a normal photodiode would produce a signal, which would be comparable to or lower than the noise produced by an amplifier. Use of the APD increases the signal-to-noise ratio of the signal and thus increases the precision of the measurement. However, it should be clear to those skilled in the art that any electrical device that is capable of outputting an electrical signal corresponding to the intensity of light illuminating it would be suitable. For example, in an alternative embodiment the APD could be replaced by a photo-multiplier tube (PMT).

Figure 3:
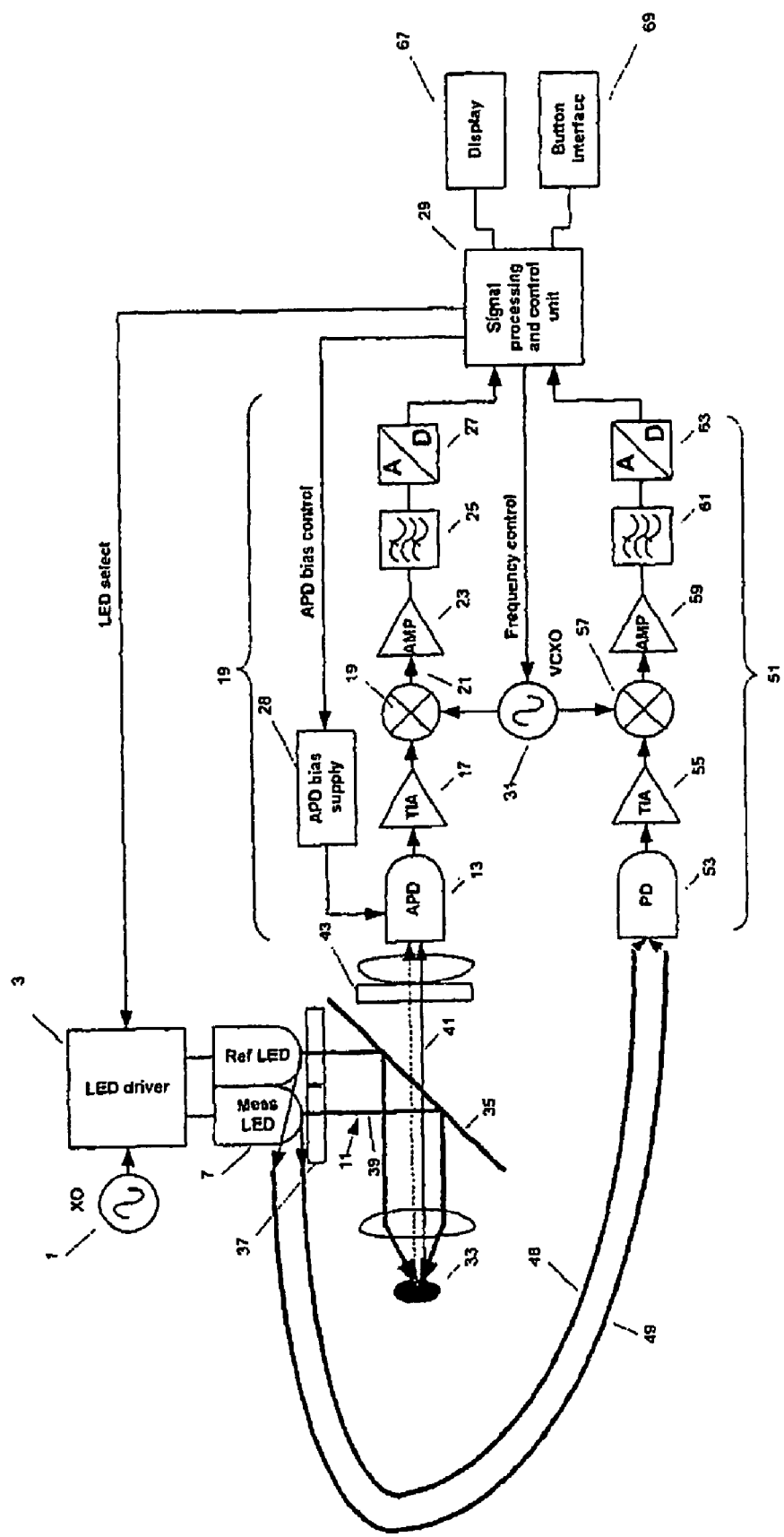
FIG. 3 is a schematic diagram of a second embodiment of the present invention.

Alternatively, a second fluorescent sample is provided at the sample location. In this embodiment shown in FIG. 3, it is arranged so that the second fluorescent sample is excitable only by light passing along the dummy measurement path. This can be achieved by emitting light of the appropriate wavelength for excitation from the reference LED. Furthermore, a filter may be provided in the dummy measurement path that allows only light of the relevant wavelength for excitation of the second fluorescent sample to pass through.

A dichroic beam splitter 34 having two reflection bands and two transmission bands is used to selectively allow light to be reflected from the light sources to the sample location and for allowing only the relevant fluorescence to pass from the sample location to the measurement circuit. Similarly, the emission filter 43 has two transmission bands to allow the fluorescent light emitted from both fluorescent samples to pass through.

Figure 4A:
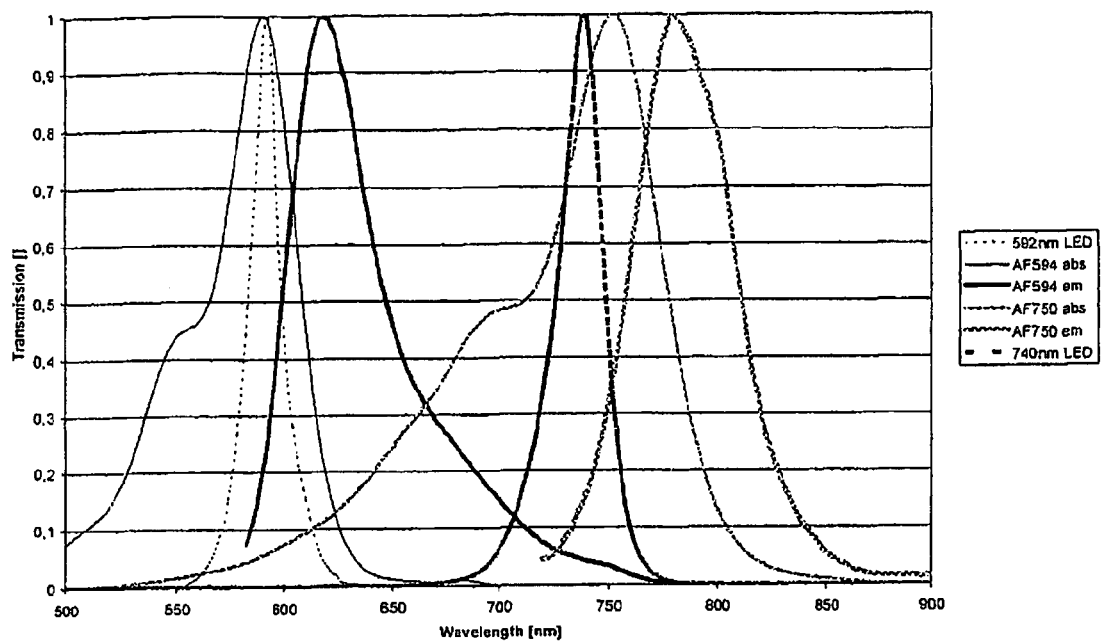
FIGS. 4A and 4B are graphs showing the excitation spectra of the first and second light sources, together with graphs of the spectra of the excitation filters, the beam splitter and the emission filter.
Figure 4B:
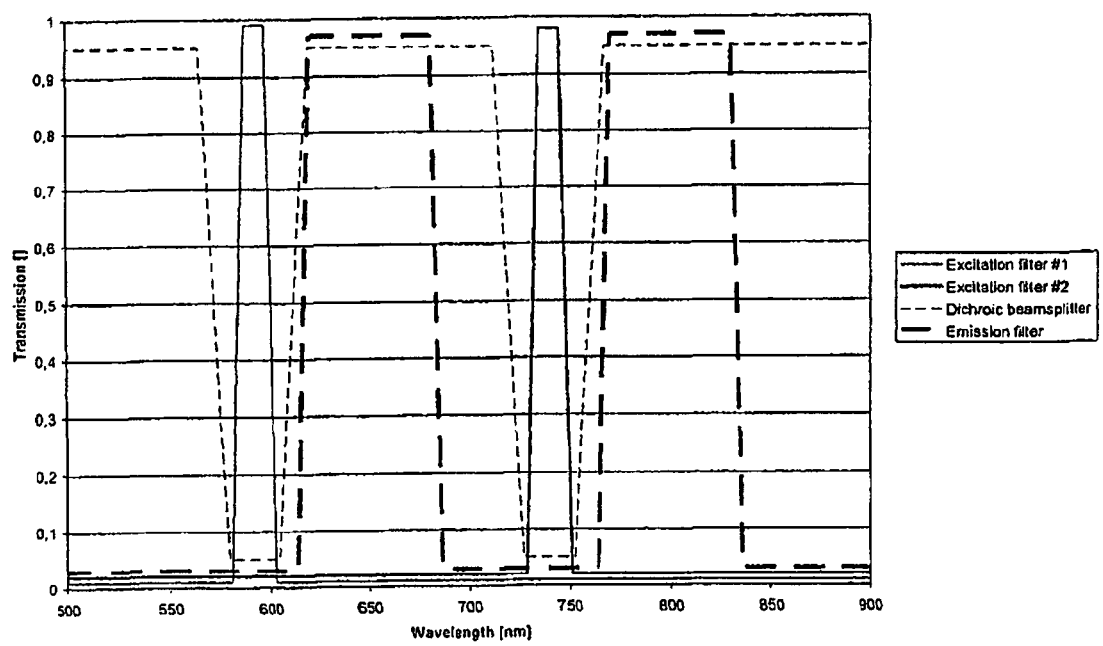

An example of wavelengths that may be appropriate is shown in FIGS. 4A and 4B. In this example, light emitted from the first LED has a wavelength of 592 nm. As can be seen, the fluorescent sample has an absorption spectrum around this wavelength, and the corresponding emission spectrum from the first fluorescent sample is based around a slightly larger wavelength. Similarly, the light emitted from the second LED has a wavelength of approximately 700 nm. The second fluorescent sample has an absorption spectrum around this sample wavelength and the corresponding emission spectrum is based around a slightly larger wavelength.

FIG. 4B shows the transmission characteristics of corresponding filters. The two bands of wavelength of light reflected by the dichroic beam splitter can be seen to correspond with the wavelengths of light emitted from, the respective LEDs, that is, at approximately 592 nm and 740 nm. As shown in FIG. 4B, these frequencies fall outside the transmission band of the dichroic beam splitter and as such, light corresponding to these wavelengths is reflected. Similarly, the two transmission bands of the dichroic beam splitter correspond with the wavelengths of the fluorescent light emitted from both fluorescent samples. Finally, the transmission bands of the emission filter also correspond to the wavelengths of the fluorescent light emitted from both samples.

In the embodiments described above, the reverse biased high voltage is provided by an APD bias supply 28 that is controlled by the signal processing and control unit 29. The signal processing and control unit 29 is also responsible for operating the further crystal oscillator 31. The waveform output from the further oscillator is also generated by means of direct digital synthesis. It would be preferred to have the same clock driving both direct digital synthesiser units. This clock is provided by the signal processing and control unit 39 such that the two oscillators are implemented as two parallel direct digital synthesisers. A sinusoidal signal from the further crystal oscillator is fed into the mixer 19, 57 of each of the sample circuit 15 and the reference circuit 51. If the optical signals input into each of the opto-electric converters 13, 53 of the sample circuit 15 and the reference circuit 53 are sinusoidal, the output from the mixer will be represented by the following equation:

$$Y(t)=A1*\sin(\omega 1*t)*A2*\sin(\omega 2*t+\phi 2)=A1*A2*\cos((\omega+\omega 2)*t+\phi 2)-A1*A2*\cos((\omega 2-\omega 1)*t+\phi 2)$$

In the present application, the mixers are used for down-mixing the signal to a frequency range which can be handled. The signal is therefore low pass filtered, which reduces the equation to:

$$Y(t)=-A1*A2*\cos((\omega 2-\omega 1)*t+\phi 2)$$

It is expected that as the optical signals fed into the opto-electric converters of both the sample circuit 15 and the reference circuit 51 originate from the same light source, the frequency of the optical signals incident upon the opto-electric converters 13, 53 should be the same.

In one embodiment, the further crystal oscillator 31 is arranged to oscillate at the same frequency as the optical signal incoming to the sample and reference circuits respectively. This is known as homodyne detection. This type of detection results in a signal output that is proportional to the phase difference between the signals. In this embodiment, the amplitude of the final signal has some mathematical relationship with the difference in phase. For $\omega 1=\omega 2$, the equation above the low pass filtered signal is reduced to:

$$Y(t)=-A1*A2*\cos(\phi 2)$$

Therefore, following conversion of the analogue signal to a digital signal, it would be possible to use these corresponding amplitudes to perform calculations to derive any shift in phase caused by the fluorescent sample 33.

Where there is a fixed difference in the frequency of the signal output from the further oscillator 31 and that of the optical signal incident upon the opto-electric converters 13, 53, this is known as heterodyne detection. The heterodyne principal is based on modulation of the light sources (measurement light source 5 and reference light source 7) with a frequency f. The gain of the signal in the sample circuit 15 and the reference circuit 51 is modulated with a frequency:

$$f+df \text{ or}$$

$$f-df$$

As stated above, this results in a down-conversion of the signals, but maintains the phase difference between the two branches. f is typically in the range of a few megahertz up to 200 megahertz. df is typically in the range of 100 to 1000 Hz, although in principle, 1 Hz up to a few LMHz would be suitable. The high frequency component is eliminated by the band pass filters 25, 61 to reduce noise in the sample circuit 15 and the reference circuit 51 respectively. As previously, the digital signals output from the analogue to digital converters 27, 63 can be processed by the signal processing and control unit to determine the shift in phase of the respective signals. This may be done in three stages:

1) determine the phase lag between the signal received in the sample circuit and the signal received in the reference circuit for the sample measurement;
2) determine the phase lag between the signal received in the sample circuit and the signal received in the reference circuit for the reference measurement; and
3) subtract the two results from each other.

If the drift in phase caused by the electronic circuitry, including the LEDs and the LED drive electronics, is negligible when comparing the shift in phase during operation of the first light source and operation of the second light source, the operation may be described by the following equations:

The constant phase lag and phase drift in the electronics are as follows:

LED driver and measure LED $$\phi ml+\Delta\phi ml$$

LED driver and reference LED $$\phi rl+\Delta\phi rl$$

measurement branch detector chain $$\phi sd+\Delta\phi sd$$

Reference branch detector chain $$\phi rd+\Delta\phi rd$$

The phase lag introduced by the fluorophore is $$\phi fl$$

Phase measurement on fluorophore gives the following equation (excitation with measure LED, phase in measurement branch minus phase in reference branch):

$\phi ml+\Delta\phi ml+\phi fl+\phi sd+\Delta\phi sd-(\phi ml+\Delta\phi ml+\phi rd+\Delta\phi rd)$ This may be reduced to $\phi fl+\phi sd+\Delta\phi sd-\phi rd-\Delta\phi rd$ The respective reference phase measurement gives the following equations (excitation with reference LED, phase in measurement branch minus phase in reference branch):

$\phi rl+\Delta\phi rl+\phi sd+\Delta\phi sd-(\phi rl+\Delta\phi rl+\phi rd+\Delta\phi rd)$ This may be reduced to $\phi sd+\Delta\phi sd-\phi rd-\Delta\phi rd$ The phase lag induced by the fluorophore is calculated by subtracting fluorophore and reference measurement:

$\phi fl+\phi sd+\Delta\phi sd-\phi rd-\Delta\phi rd-(\phi sd+\Delta\phi sd-\phi rd-\Delta\phi rd)=\phi fl$ It is observed that constant phase offset and drift induced by the electronics is cancelled. The concentration of the analyte is calculated by the signal processing and control unit 29 based upon a pre-calculated calibration curve. The result is displayed on the display 67 as a number.

Figure 6:
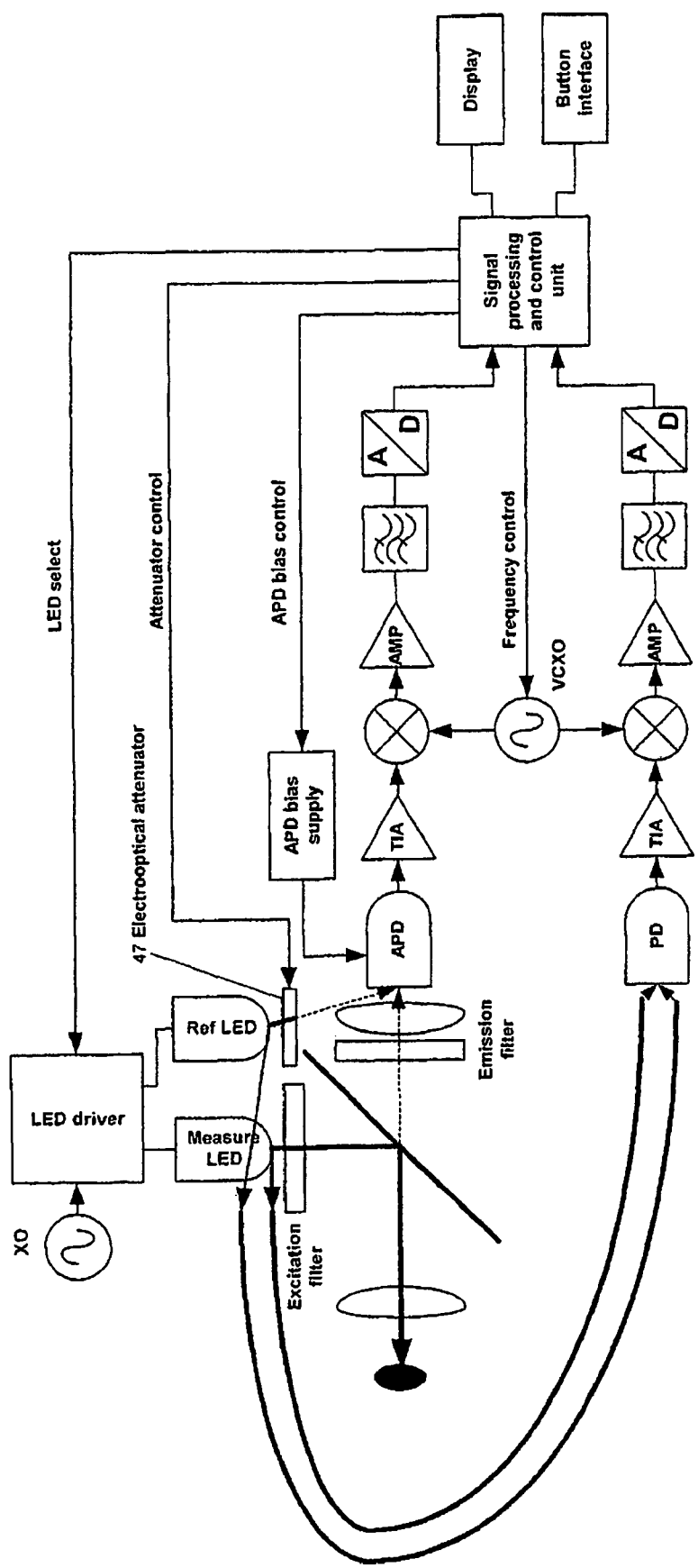
FIG. 6 is a further schematic of the embodiment shown in FIG. 5 with additional circuitry.

The calibration curve is the result of phase offset induced by the difference in optical path length, if any, and the dose response curve, which is characteristic for the assay chemistry. An example on a calibration curve is shown in FIG. 6. If batch variations are present on the assay chemistry, calibration parameters may be keyed in by the use of a simple user interface 69, e.g. consisting of two buttons. Said buttons may furthermore be used to initiate a measurement or to set-up a sequence of measurements as required for continuous blood glucose monitoring. In the case of blood glucose monitoring, calibration of the system may be done by performing a reference glucose measurement with an ordinary discrete blood glucose meter and keying in the result. The calibration is then done by the device using the reference measurement and the corresponding measurement performed by the device.

An alternative embodiment of the system described above is illustrated in FIGS. 5 and 6 where during operation of the reference LED 5, the light signal 45 emitted is guided directly to the APD 13. The light 45 is guided to the APD 13 of the measurement circuit 15 by means of a light guide 65 or by a free optical path. The embodiment shown in these diagrams does not measure absolute phase as there is a significant difference in the path the reference light follows before illuminating the measurement branch circuitry. The phase measured during operation of the reference LED 7 may differ from the phase measured during operation of the measurement LED 5 by a small constant offset induced by the difference between the optical path lengths 11, 9.

Therefore, while it is preferable for the paths to be the same, or almost the same, it is not essential. For example, at a modulation frequency of 60 MHz, a variation in measurement path length of 1.5 mm produces a phase change of approximately 0.1°. The phase change is inversely proportional to the modulation frequency, which increases the demands on the stability on the path length at 1 GHz (0.1 mm gives approximately 0.1°). It is preferable to have a variation below 1.5 mm in path difference in the measurement path.

Figure 5:
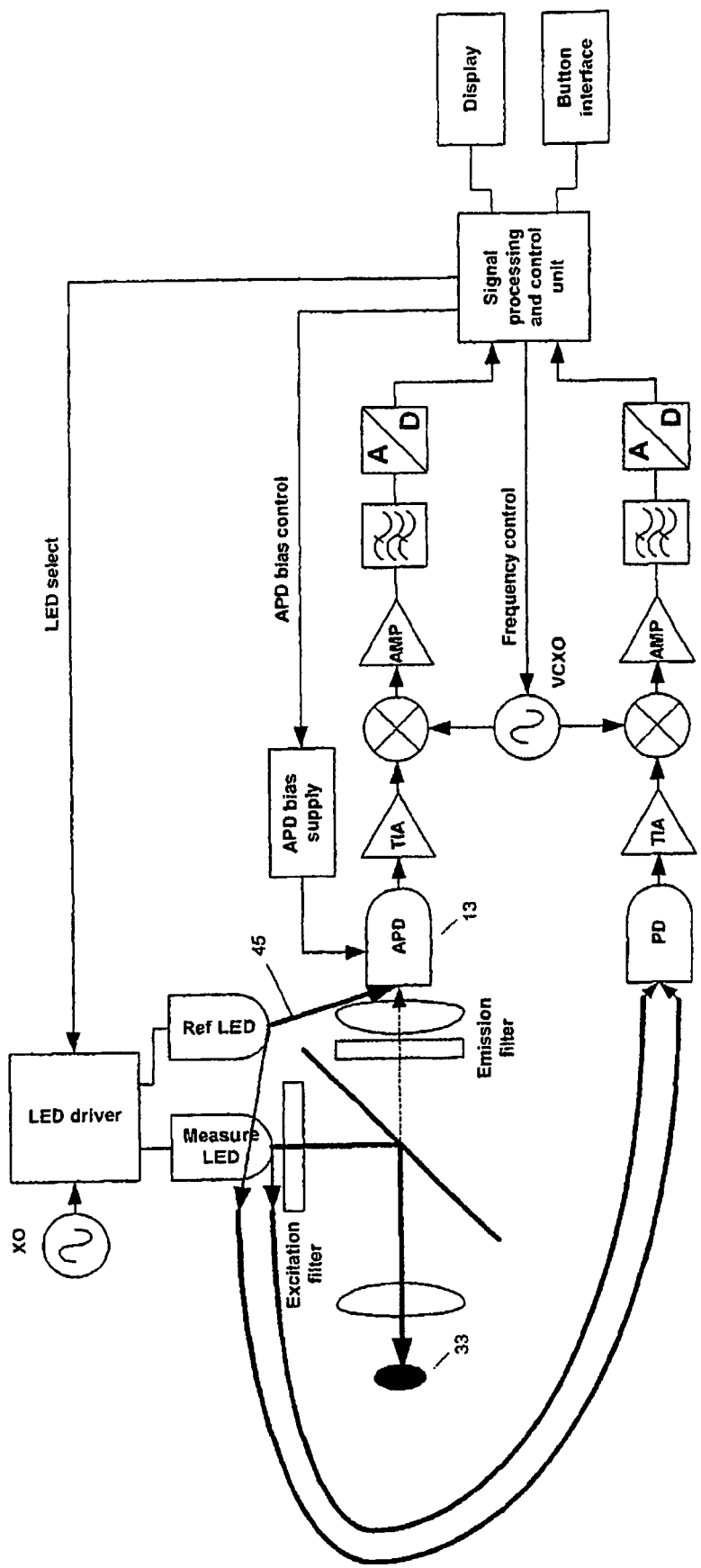
FIG. 5 is a schematic diagram of a third embodiment of the present invention.

In the embodiment shown in FIG. 5, where the light signal from the reference LED 7 travels direct to the electro-optical converter 13 of the sample circuit 15, it may be desired to adjust the intensity of the detected light. This may be necessary in order to allow the sample circuit 15 to operate under similar conditions as when receiving light emitted by the fluorescent sample 33. One way in which this may be done is by adjusting the drive current to the reference LED 7. However, this would affect the conditions in the reference branch as the output from the reference LED 7 would be different. It is therefore preferable to maintain the light intensity in the reference branch by adjusting the intensity of the detected light from the reference LED 7 by introducing an electro optical attenuator 47 in the second optical path 9, as shown in FIG. 6.

As an example, the electro optical attenuator 47 could be a twisted nematic liquid crystal display (TN LCD), a super twisted nematic liquid crystal display (STN LCD), a digital Micro-mirror Device/Digital light processor (DMD/DLP) or a ferro electric liquid crystal display.

Figure 7:
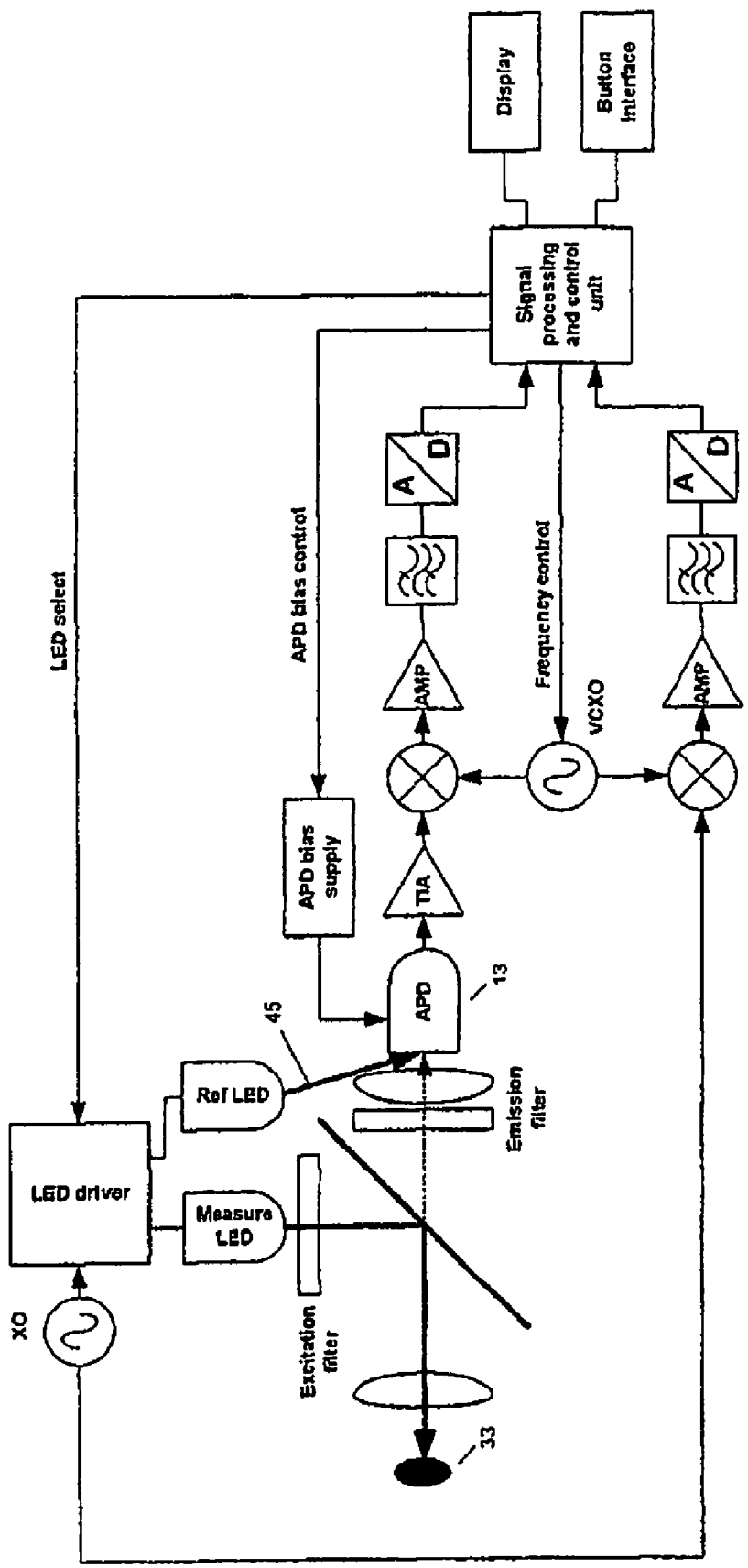
FIG. 7 is a schematic diagram of a fourth embodiment of the present invention.

In another alternative embodiment, the phase of light may be measured directly by measuring the phase of the drive current to the first and second LEDs. In this embodiment, it would not be necessary to emit light from both the first and second LEDs along a reference path to an opto-electric convertor of the reference circuit. Instead, and as shown in FIG. 7, the phase is measured directly from the LED driver and input to the mixer of the reference circuit.

A system as described can be used to determine the concentration of analyte present in a competition assay. In a competition assay, FRET can occur as a result of a FRET active molecule combining with a competition agent that is also FRET active. The shift in phase detected is based upon the average lifetime of the detected fluorescence. The system described above is calibrated by directing light from the measurement LED 5 to a solution having a known concentration of analyte. Information derived from the signals in the various circuits can be used to create a calibration curve. During real time operation, a predetermined concentration of FRET active material and competition agent are provided. FRET is detected by calculating the shift of phase caused in the light received by the measurement electronic circuit. As the amount of FRET corresponds to the amount of analyte present, this shift of phase is compared with the calibration curve to enable determination of the concentration of analyte present.

One application of such a system would be in the measurement of blood glucose concentrations. In these circumstances, a fluorophore is linked to a glucose binding molecule and an energy acceptor is linked to a glucose analogue. As long as the glucose analogue is bound to the glucose binding molecule, the maximum possible FRET will occur. When glucose is present, it competes with the glucose analogue for the binding site and displaces the acceptor molecule. At this time, less FRET occurs.

Where two fluorescent samples are required for obtaining measurements, in addition to linking a fluorophore to a glucose binding molecule, a further reference fluorophore, which is not affected by the glucose concentration, can be provided as the second fluorescent sample. In this case, if the second fluorescent sample has a known effect on the intensity and phase of the resultant fluorescence, then it can be used as a reference from which to calculate the shift in phase caused by the FRET.

When taking measurements, it is possible that other fluorophores found in the skin, could cause interference if they emit fluorescent light upon radiation by the excitation light. This additional interference would make it difficult to detect the shift in phase caused by FRET. In these circumstances, it would be preferable to adapt the system to enable light of two or more different modulation frequencies to be alternately emitted from the reference and measurement LEDs. The additional frequencies would preferably be in a range similar to that of the first. The modulation frequencies typically but not necessarily differ from each other with a factor of two or more depending on the fluorophores that contribute to the phase changes. In the case of heterodyne detections. the frequency difference between the two oscillators is kept constant so that no further processing electronics would be required.

As the different fluorophores would each have different lifetimes, this would cause varying degrees of shift in phase of the respective signals. In addition, each fluorophore would cause a different reduction in amplitude of the fluorescent signal. Using light of two or more different modulation frequencies would enable further calculations to be made based upon the changes in phase and amplitude of the fluorescent signal by the signal processing and control unit 29. In this respect, the circuitry required for detecting the difference in amplitude would be the same as that for detecting a shift in phase. The beat frequency fed into the respective analogue to digital converters 27, 63 in each of the measurement and reference circuits would have an amplitude corresponding to the intensity of the fluorescent signal. These digitised signals would be fed into the signal processing and control unit to enable determination of the shift in frequency caused by FRET. For each additional lifetime that may be measured, a measurement at a different frequency would be required. At each different frequency, a measurement should be taken with both the measurement LED and the reference LED active.

This system could also be used in Fluorescence Lifetime Imaging Microscopy (FLIM). FLIM enables the discrimination of fluorescence emitted from different fluorescent materials, that exhibit similar absorption and emission properties, but that show a difference in fluorescence lifetime. Fluorescence lifetime is calculated by measuring the phase shift of fluorescence and the reduction in its amplitude. In lifetime imaging acquisition, a number of images are acquired, where the phase will vary depending on the lifetime of the fluorescence at that particular point. Signals obtained as a result of FLIM will be subject to similar factors that may cause drift of the phase of the signal. Therefore, to relate this relative lifetime image to an actual lifetime image a reference is necessary. The system described above would be capable of performing consecutive measurements as described above for each pixel or line of the image.

It is appreciated that variations in, and modifications to, the embodiments described and illustrated may be made within the scope of the appended claims.

The invention claimed is:

1. Apparatus for measuring a phase shift induced in a light signal by a sample, the apparatus comprising:
    a first light source for emitting a light signal along a measurement optical path, wherein the measurement optical path includes a sample location;
    a second light source for emitting a light signal along a dummy measurement optical path, the first and second light sources being arranged for alternate operation whereby in use during the measurement of said phase shift the first and second light sources are switched on and off alternately so that light signals are emitted alternately from the first and the second light sources and so that activation of the second light source both precedes and follows activation of the first light source;
    a measurement electronic circuit for receiving the light signals from the measurement and dummy measurement optical paths, the measurement electronic circuit being arranged to provide outputs separated in time which are respectively indicative of the phase of the light signals received from each of the measurement and dummy measurement optical paths, wherein in use a phase shift is induced in light in the measurement optical path by a sample in said sample location such that the phase of light of the first light source received from the measurement optical path is different to the phase of light emitted from the first light source;
    a reference electronic circuit for receiving a signal indicative of the phase of the light signals emitted by the first and second light sources;
    circuitry to compare the phase of light indicated by the output of the measurement electronic circuit responsive to the first light source with the phase of light indicated by the reference electronic circuit to provide an output indicative of a first measured phase difference and to compare the phase of light indicated by the output of the measurement electronic circuit responsive to the second light source with the phase of light indicated by the reference electronic circuit to provide an output indicative of a second measured phase difference, and circuitry to apply a correction to the first measured phase difference on the basis of the second measured phase difference to correct for errors in said first measured phase difference due to phase changes induced by said measurement and reference electronic circuits so as to obtain an improved measurement of the shift in phase induced in the light of the first light source by the sample.

2. Apparatus as claimed in claim 1, wherein the first light source further emits a light signal along a reference optical path, and the second light source further emits a light signal along a dummy reference optical path, wherein the reference electronic circuit further comprises means for receiving the light signals from the reference and dummy reference optical paths, the reference electronic circuit being arranged to provide outputs separated in time which are respectively indicative of the phase of the light signals received from each of the reference and dummy reference optical paths.

3. Apparatus as claimed in claim 1, wherein the measurement optical path comprises a beam splitter receiving light from said first light source and reflecting said light toward said sample location and receiving fluorescence emission light in use emitted from said sample location and transmitting said fluorescence emission light to said measurement electronic circuit.

4. Apparatus as claimed in claim 3, wherein the dummy measurement path comprises said beam splitter, the beam splitter being arranged to receive light from the second light source, reflect said light toward said sample location, receive said light reflected from said sample location and transmit the light to said measurement electronic circuit.

5. Apparatus as claimed in claim 4, wherein the dummy measurement optical path further comprises the said emission filter for selecting a wavelength of light comparable to the wavelength of fluorescent light emitted from the sample location.

6. Apparatus as claimed in claim 3, wherein light from the second light source is not received by the beam splitter and is guided directly to the measurement electronic circuit.

7. Apparatus as claimed in claim 3, wherein the dummy measurement path comprises said beam splitter, and the beam splitter is arranged to receive light from said second light source, reflect said light towards said sample location, receive fluorescence emission light in use emitted from said sample location and to transmit said fluorescence light to said measurement circuit.

8. Apparatus as claimed in claim 1, wherein said measurement optical path comprises an excitation filter arranged to select a wave length of light suitable for exciting a first fluorescent sample at said sample location and an emission filter suitable for selecting a wave length of fluorescent light emitted from said sample location.

9. Apparatus as claimed in claim 1 wherein an oscillator is coupled to each of the first and second light sources to produce light signals of oscillating intensity.

10. Apparatus as claimed in claim 1, wherein the light in the dummy measurement path does not include a wave length of light suitable for exciting the first fluorescent sample.

11. Apparatus as claimed in claim 1, wherein means are provided for guiding light from the first and second light sources along the reference and dummy reference optical paths respectively to an opto-electric converter of the reference circuit.

12. Apparatus as claimed in claim 1, wherein light modulated at two or more different frequencies are alternately generated and output from each of the first and second light sources consecutively to enable further calculations.

13. Apparatus as claimed in claim 1 for use in a glucose measuring system, wherein the sample has fluorescence characteristics which can be modulated by the concentration of glucose present in the sample.

14. A method of measuring a phase shift induced in a light signal by a sample, comprising the steps of:
  emitting a first light signal along a measurement optical path, wherein the measurement optical path includes a sample location;
  emitting a second light signal along a dummy-measurement optical path, the first and second light signals being emitted alternately such that during the measurement of said phase shift the first and second light sources are switched on and off alternately so that light signals are emitted alternately from the first and the second light sources and so that activation of the second light source both precedes and follows activation of the first light source;
  receiving light signals from the measurement and dummy-measurement optical paths in a measurement electronic circuit;
  providing outputs separated in time from the measurement electronic circuit, wherein the outputs are respectively indicative of the phase of the light signals received from each measurement and dummy-measurement optical path;
  receiving a signal indicative of the phase of the first and second light signals in a reference electronic circuit;
  comparing the phase of light indicated by the output of the measurement electronic circuit and responsive to the first light signal with the phase of light indicated by the reference electronic circuit;
  providing an output indicative of the first measured phase difference;
  comparing the phase of light indicated by the output of the measurement electronic circuit in response to the second light signal with the phase of light indicated by the reference electronic circuit;
  providing an output indicative of a second measured phase difference;
  applying a correction to the first measured phase difference on the basis of the second measured phase difference to correct errors in said first measured phase difference due to phase changes induced by said measurement and reference electronic circuit so as to obtain an improved measurement of the shifting phase induced in the light of the first light source by the sample.

15. A method as claimed in claim 14 further comprising:
  additionally emitting the first light signal along a reference optical path and the second light signal along a dummy-reference optical path;
  receiving the light signals from the reference and dummy-reference optical paths in the reference electronic circuit;
  outputting from the reference electronic circuit signals separated in time which are respectively indicative of the phase of each of the light signals received from the reference and dummy-reference optical paths.

16. A method as claimed in claims 14, further comprising:
  selecting a wavelength of light for the first light signal suitable for exciting a first fluorescent sample at said sample location; and
  selecting a wavelength of fluorescent light emitted from said sample location.

17. A method as claimed in claim 14, further comprising producing first and second light signals of oscillating intensity.

18. A method as claimed in claim 14, further comprising:
  receiving the first light signal emitted along the dummy measurement path in a beam splitter;
  reflecting said light toward said sample location; and
  transmitting the light to said measurement circuit.

19. A method as claimed in claim 14, further comprising:
  converting the light signal received in the measurement electronic circuit into an electrical signal corresponding to an intensity of the light signal; and
  outputting the electrical signal.

20. A method as claimed in claim 14, further comprising guiding the first and second light signals from the first and second light sources respectively along the reference and dummy reference paths to an opto-electric converter of the reference circuit.

21. A method as claimed in claim 14, further comprising modulating the signal being processed in each of the measurement electronic circuit and reference electronic circuit to produce an output representing the phase of the signal being processed.

22. A method as claimed in claim 21, further comprising:
  digisitsing the output representing the phase of the signal being processed;
  comparing the digitised signals generated during operation of each of the first and second light sources respectively;
  calculating the phase change induced by the sample; and
  outputting a result of the calculation to a display.

* * * * *